United States Patent [19]

Sparer et al.

[11] Patent Number: 5,211,951
[45] Date of Patent: May 18, 1993

[54] PROCESS FOR THE MANUFACTURE OF BIOERODIBLE POLY (ORTHOESTER)S AND POLYACETALS

[75] Inventors: Randall V. Sparer; Gaylen Zentner, both of Lawrence, Kans.

[73] Assignee: Merck & Co., Inc., Rahway, N.J.

[21] Appl. No.: 734,843

[22] Filed: Jul. 24, 1991

[51] Int. Cl.$^5$ ............................................... A61F 2/00
[52] U.S. Cl. .................................... 424/426; 424/484
[58] Field of Search ................. 424/426, 78, 487, 484; 524/500

[56] References Cited

U.S. PATENT DOCUMENTS 4,814,183  3/1989  Zentner ............................... 424/487
5,047,464  9/1991  Pogany et al. ....................... 524/500

OTHER PUBLICATIONS

D. R. Day, et al., Micromet Instruments Publication No. CA0001, "Cure Monitoring: A Comparison of Dielectric and Thermal Analysis", Micromet Instruments, Inc., 26 Landsdowne Street, Suite 150, Cambridge, MA, 02139.
LaVerne Leonard, Micromet Instruments Publication No. RP0019, "Microdielectrometry: Tiny Sensors Close the Cure Control Loop", Reprinted from Advanced Composites, Jan./Feb. 1987.
M. L. Bromberg, et al., Micromet Instruments Publication No. RP0009, "New Applicatins for Dielectric Monitoring and Control", Micromet Instruments, Inc., 26 Landsdowne Street, Suite 150, Cambridge, MA, 02139, pp. 307–311.
M. Connoly and B. Tobias, American Laboratory, Jan. (1992), 38–42.
R. W. Biernath, et al., "Dynamic Microdielectric Monitoring of Epoxy/Phenolic Cure", Department of Chemical Engineering, University of California at Berkeley, Berkeley, CA, 94720.

Primary Examiner—Thurman K. Page
Assistant Examiner—D. Colucci
Attorney, Agent, or Firm—Francis P. Bigley; Joseph F. DiPrima

[57] ABSTRACT

A process for the manufacture of bioerodible poly(ortho ester)s and polyacetals containing beneficial agents having a hydroxyl functionality of two or more and their fabrication into controlled release dosage forms having a reproducible delivery of the beneficial agent into the biological environment of use are disclosed.

11 Claims, 1 Drawing Sheet

PROCESS FOR THE MANUFACTURE OF BIOERODIBLE POLY (ORTHOESTER)S AND POLYACETALS

BACKGROUND OF THE INVENTION

Because of bioavailability, efficacy, or dosing convenience concerns, many beneficial agents are preferably administered parenterally. Since a recipient could receive several dosage forms over a lifetime, it is essential that the dosage form leave little or no undesirable residue. Bioerodible polymeric dosage forms are ideally suited for these applications, and provide the additional advantage that drug delivery from a single dosage form may effectively treat the disease state for a prolonged period.

Known bioerodible polymeric controlled release devices can be generally categorized as either encapsulated devices or matrix devices. In encapsulated devices, beneficial agent (e.g., drug) is surrounded by a polymer layer which controls release of the beneficial agent. The beneficial agent in a matrix device, however, is dissolved or suspended in the polymer matrix and diffuses through the matrix, or is released in conjunction with the dissolution, disintegration, decomposition, or erosion of the matrix.

With matrix devices, beneficial agents can be incorporated into the matrix by physical entrapment or are chemically bound to the matrix. When exposed to a biological environment of use, the polymer matrix dissolves, disintegrates, decomposes, or erodes (i.e., degrades) to release beneficial agent.

Known matrix devices in which the beneficial agent is chemically bound to the polymeric matrix are limited to compositions such as those of U.S. Pat. Nos. 4,356,166, 4,636,387, and 4,745,161, in which the beneficial agent is pendantly attached to the polymeric chains comprising the matrix rather than directly incorporated into the polymer chain backbone. Significantly, these known pendant polymer-beneficial agent schemes require a disadvantageous multi-step synthesis.

Co-pending U.S. Patent Application Ser. No. 570,742 filed Aug. 22, 1990 describes bioerodible implants which are fabricated from poly (ortho ester)s and polyacetals which may be prepared from the instant invention.

SUMMARY OF THE INVENTION

The instant invention provides a process for the manufacture of the bioerodible poly(ortho ester)s and polyacetal polymers which contain beneficial agents having a hydroxyl functionality of two or more and their fabrication into controlled release dosage forms having a reproducible rate of delivery of the beneficial agent into the biological environment of use over an extended period of time by utilizing dielectrometer measurements to follow the viscosity of the condensation reaction of the beneficial agents, the polyols and the diketene acetal or the divinyl ether.

The instant invention is a significant improvement in the reproducibility of manufacture of these polymers. The process is controlled in real-time from dielectrometer measurements. The dielectrometer read-out indicates: i) when reagents are to be added to the polymerization mixture; ii) when the polymerization mixture is to be transferred from the mixer into the molds; and iii) when the molded mixture is cured and should be removed from the curing oven.

The environment of use may be any anatomical site where the dosage form may be located to elicit the desired pharmacological response. Specifically, dosage forms of the present invention are formed by condensing beneficial agents such as drugs having a hydroxyl functionality of at least two and, if desired, other polyols, with diketene acetals or divinyl ethers (where the term polyol is employed throughout this specification, it implies a molecule with 2 or more hydroxyl groups). The resultant bioerodible polymeric dosage form comprises either a poly(ortho ester) or a polyacetal. An important feature of the polymeric dosage forms of the instant invention is that a statistically significant portion of the amount of monomeric beneficial agent is covalently incorporated into the resultant bioerodible polymer chain backbone, i.e., the beneficial agent is incorporated into the polymer backbone by means of hydrolytically labile ortho ester or acetal bonds.

U.S. Pat. No. 4,304,767 describes the synthesis of poly(ortho ester)s by condensation of diketene acetals and polyols. U.S. Pat. Nos. 4,150,108 and 4,221,779 describe condensation of divinyl ethers and polyols to form polyacetals. While none of these patents suggest the use of a beneficial agent (drug) as a polyol condensation monomer, their general disclosure of poly(ortho ester) and polyacetal synthesis, is incorporated herein by reference.

Representative examples of biologically active beneficial agents are drugs having two or more hydroxyl groups that can serve as condensation monomers in the synthesis of the bioerodible dosage form of the present invention and include anthelmintic agents from the general groups of compounds collectively known as the avermectins and milbemycins, including specific example compounds such as ivermectin, moxidectin, milbemycin-5-oxime, 4''-epi-acetylamino-4''-deoxyavermectin Bla/Blb, and 22,23-dihydro-13-O-((2-methoxyethoxy)methyl)avermectin-Bl-aglycone and nemadectin. Representative of another type of anthelmintic is the compound bithional. Other beneficial agents possessing two or more hydroxy groups that may be covalently incorporated into the polymer matrix are: narcotics and narcotic antagonists such as morphine, nalorphine, naloxone, and naltrexone; antihistamines such as terfenadine; adrenergic agonists such as phenylephrine, terbutaline, albuterol, isoproterenol; adrenergic blockers such as nadolol, pindolol; sedative hypnotics such trichlofos, chlorhexadol; centrally acting agents such as mephenesin; analeptics such as picrotin; antiparkinson agents such as L-dopa/carbidopa; steroids such as digoxin, prednisone, triamcinolone, dexamethasone, beclomethasone, estradiol, ethinyl estradiol, fluoxymesterone; coronary vasodilators such as dipyridamole; anticoagulants such as dicumarol and heparin; antihypertensives such as $\alpha$-methyldopa and labetalol; antiinflammatory/antirheumatic agents such as osalazine and aurothioglucose; cholesterol reducing agents such as probucol and HMG-CoA reductase inhibitors such as pravastatin, or lovastatin and simvastatin in the open hydroxy acid form; antibiotics such as doxycycline, minocycline, erythromycin, clindamycin, gentamicin, tobramycin, spectinomycin, mithramycin, rifampin; antifungal agents such as amphotericin B, nystatin; antiviral agents such as vidarabine, idoxuridine; bone growth promotants such as prostaglandin $E_2$; anticancer agents such as streptozocin, doxorubicin, vinca alkaloids; and, vitamins such as pyridoxamine and riboflavin. The above list is not meant to be exhaustive. Any beneficial agent with two or more hydroxyl groups is within the scope of the invention. It is known to the art that beneficial agents can be synthesized as various forms of prodrugs which may contain two or more hydroxyl groups and, therefore, are included. Depending on its specific therapeutic role the beneficial agent may provide prophylactic therapy and/or treatment of an existing condition.

The following schemes illustrate the condensation reaction of beneficial agent and other monomeric polyols with diketene acetals and divinyl ethers to form bioerodible poly(ortho ester)s and polyacetals, respectively:

SCHEME 1

Poly(ortho ester)s

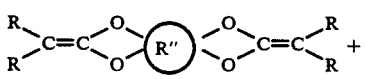

$$D(OH)_a + R'(OH)_b \longrightarrow (A-D)_x(A-R')_y(A-R')_z$$
$$\qquad\qquad\qquad\qquad\qquad\qquad\qquad\qquad\qquad |$$
$$\qquad\qquad\qquad\qquad\qquad\qquad\qquad\qquad\qquad A-$$

R is H, alkyl, aryl (R groups may be the same or different);
R" is quadrivalent carbon or grouping;
$D(OH)_a$ is beneficial agent or drug;
$R'(OH)_b$ is polyol;
a is 2 or greater;
b is 2 or greater;
A is

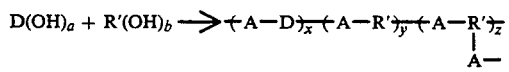

x is mer units with (a=2)
y is mer units with (b=2)
z is mer units with (b=3) (R' in z-type mer units may be substituted in part by D in cases where D possesses 3 or more hydroxyls).

SCHEME 2

Polyacetals

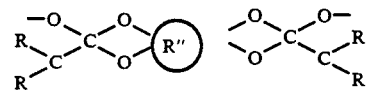
$+ D(OH)_a + R'(OH)_b \longrightarrow$ $$(A-D)_x(A-R')_y(A-R')_z$$
$$\qquad\qquad\qquad\qquad\qquad |$$
$$\qquad\qquad\qquad\qquad\qquad A-$$

R is covalent linkages or alkylene which may optionally contain heteroatoms (see U.S. Pat. Nos. 4,150,108 and 4,221,779);
$D(OH)_a$ is beneficial agent or drug;
$R'(OH)_b$ is polyol;
a is 2 or greater;
b is 2 or greater;
A is

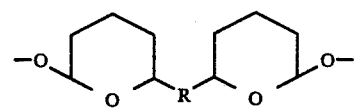

x is mer units with (a=2);
y is mer units with (b=2);
z is mer units with (b=3) (R' in z-type mer units may be substituted in part by D in cases where D possesses 3 or more hydroxyls.)

DETAILED DESCRIPTION OF THE INVENTION

Figure 1:
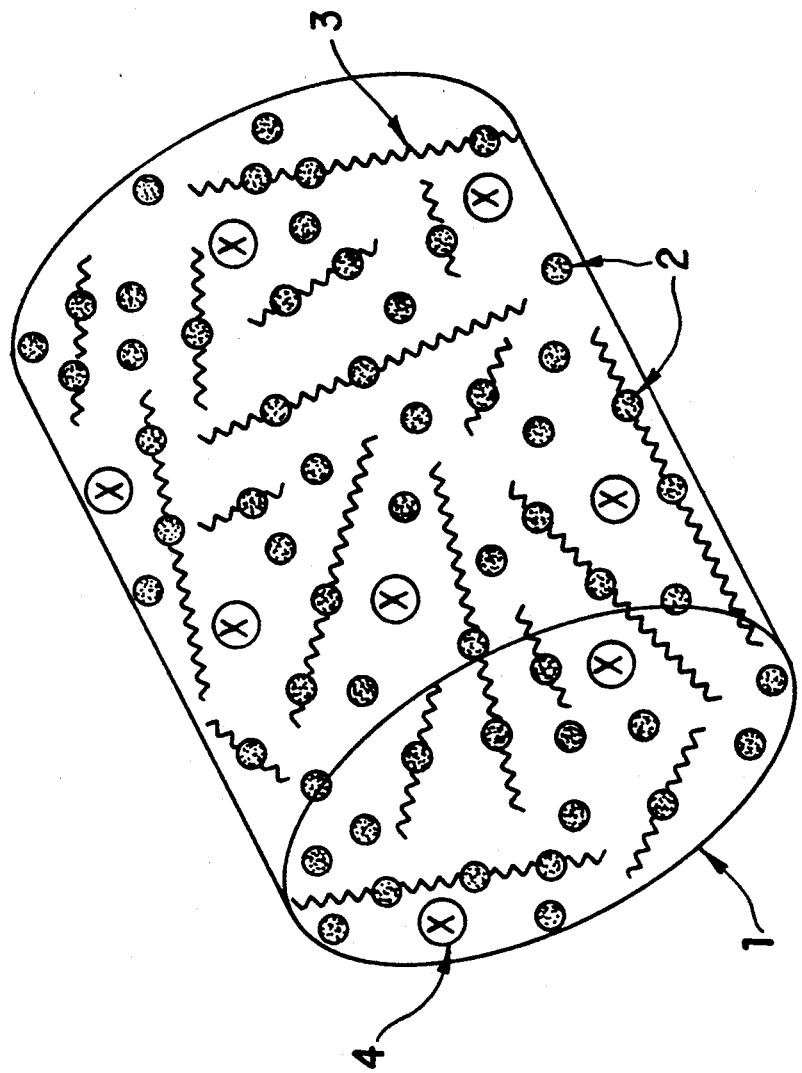
FIG. 1 depicts a rod-shaped implant manufactured in accordance with the present invention.

The instant invention is directed to a process for the manufacture of a bioerodible poly(ortho ester) or polyacetal containing a beneficial agent having a hydroxyl functionality of two or more which comprises the condensation of:
(a) a diketene acetal or a divinyl ether;
(b) the beneficial agent; and
(c) a polyol monomer
in the presence of a poly(ortho ester) bond stabilizer or a polyacetal bond stabilizer wherein: (i) the beneficial agent and the stabilizer are added to the polyol and the resultant mixture stirred unitl the viscosity (or conductivity$^{-1}$) remains essentially constant, as measured by a dielectrometer; (ii) the diketene acetal or divinyl ether is then added to the stirred mixture and condensation allowed to proceed until the viscosity (or, conductivity$^{-1}$) of the poly(ortho ester) or polyacetal is sufficiently high, as measured by a dielectrometer, to keep the stabilizer uniformly suspended; and (iii) the reaction mixture is subsequently transferred to a mold and cured in an oven, where curing is allowed to proceed until the viscosity (or, conductivity$^{-1}$) of the mixture is sufficiently high to be fully cured, while preventing excess degradation (decrease in viscosity) from over-curing.

The instantly produced polymers may be shaped in numerous geometric configurations. A rod-shaped device, 1, is illustrated in FIG. 1. When sized at 0.5 mm to 5 mm diameter and 0.5 to 10 cm in length this shape is readily suited for implantation, although larger and smaller dimensions are within the scope of the disclosure. The beneficial agent (frequently a drug), 2, is to a substantial degree covalently incorporated into the backbone of the polymer chains comprising the bioerodible matrix, 3, with a portion of the total drug also dispersed throughout the matrix. Other additives, 4, such as stabilizers, antioxidants and catalysts may be optionally included. The bioerodible controlled release dosage form is implanted intramuscularly, subcutaneously or intraperitoneally. If desired, more than one implant may be inserted.

In a preferred embodiment, a poly(ortho ester) implant is synthesized by a condensation reaction of polyol monomers, including the polyol anthelmintic drug, ivermectin, with a diketene acetal to form a potent implantable dosage form useful against various developmental stages of *Dirofilaria immitis*, a filarial parasite and causative organism of canine heartworm disease. Specifically, ivermectin and various combinations of other polyols such as 1,6-hexanediol, 1,7-heptanediol, tetraethylene glycol, triethylene glycol, and 1,2,6-hexanetriol were covalently reacted with the diketene acetal 3,9-bis(ethylidene)-2,4,8,10-tetraoxaspiro[5,5]undecane (viz., DETOSU) to form a poly(ortho ester) matrix. Ivermectin is a polyol with three hydroxyl groups, and therefore reacts with the DETOSU. A significant portion (20 to 60%) of the ivermectin was covalently incorporated into the poly(ortho ester) chains. This dosage form provides prophylactic levels of ivermectin for periods ranging from three to fifteen months with a single dose. This dosage form can be administered to a recipient by simple subcutaneous injection. This implant is biodegradable and completely erodes within the animal while releasing drug, thus ensuring that accumulation of implants is minimized with repeat dosings.

Anthelmintic beneficial agents other than ivermectin, such as C-076 avermectin derivatives, milbemycins and closely related compounds such as nemadectin and moxidectin, which contain two or more hydroxyl groups can be utilized in the instant preferred embodiment of the invention. These agents are disclosed in the following U.S. Pat. Nos. 4,199,569, Chabala et al, Selective Hydrogenation Products (Ivermectin); 4,200,581, Fisher et al, Alkyl Derivatives; 4,201,861, Mrozik et al, Acyl Derivatives; 4,203,976, Fisher et al, Carbohydrate Derivatives; 4,206,205, Mrozik et al, Monosaccharide and Aglycone Derivatives; 4,289,760, Mrozik et al, 23-keto Derivatives; 4,427,663, Mrozik et al, 4"-keto and 4"-Amino Derivatives, including 4"-epi-acetylamino-4"-deoxyavermectin Bla/Blb; 4,469,682, Mrozik, Phosphate Esters; 4,530,921, Mrozik, Epoxide Derivatives; Re 32006, Chabala et al, 13-Halo and 13-Deoxy Derivatives; 4,547,491, Mrozik et al, C8a Oxo Derivatives; Re 32034, Chabala et al, 13-Halo and 13-Deoxy Derivatives; 4,579,864, Linn et al, 13-Keto, 13-Imino and 13-Amino Derivatives; 4,581,345, Wyvratt, 8,9-Cyclopropyl Derivatives; 4,587,247, Linn et al, 13-Poly alkoxy Derivatives, including 22,23-dihydro-13-O-((2-methoxyethoxy)methyl)avermectin-Bl-aglycone; 4,622,313, Wyvratt, O-Sulfate Derivatives; 4,806,527, Christensen et al, Δ26,27-Alkyl Derivatives; 4,831,016, Mrozik et al, Reduced Derivatives; 4,833,168, Wyvratt, Reformatsky Adducts; 4,873,224, Linn et al, 4',4" Semicarbazone, hydrazone etc. Derivatives; 4,874,749, Mrozik, 4"-M-methyl Amino Derivatives; 4,895,837, and Mrozik et al, Δ23,24 Derivatives; 4,897,383, Sinclair, 3',3" Des methoxy Derivatives; and 3,950,360, Aoki et al, Milbemycin natural products. The following European patents also apply: EP 110,667, Ide et al, Milbemycin-5-oxime derivatives; EP 214,731, Gibson et al, 25-substituted milbemycin compounds; and EP 170006, 25-substituted milbemycin compounds; and EP 170006, Wood et al, 25-substituted milbemycin compounds.

The avermectin and milbemycin compounds described in the above references, and which may be incorporated as a beneficial agent in the implant of the present invention, are particularly effective against endo or ecto parasites, of animals and man, that feed on or are associated with blood, body secretions or tissues, such as developing larvae of *Dirofilaria immitis* in dogs and cats. Other endoparasites of dogs and cats particularly hookworms, *Ancylostoma caninum, Ancyclostoma tubaeforma, Ancylostoma braziliense,* and *Uncinaria stenocephala,* and whipworms *Trichuris vulpis* are likely targets. Ascarids, such as *Toxocara canis, Toxocara cati,* and *Toxascaris leonina,* are also potential targets, as are the threadworms *Strongyloides stercoralis* and lungworms *Capillaria* sp. and *Aelurostrongylus* sp. Ecto parasites particularly ear mites *Otodectes cynotis,* other mites, fleas and ticks may also be affected.

The implant can be synthesized and fabricated as either a linear polymer or crosslinked polymer erodible matrix. The techniques used in fabricating the implant will vary. Linear (thermoplastic) polymers can be synthesized and then reheated at a later time for compounding with additives (e.g., stabilizers and antioxidants). This mixture can then be reheated at a later time for molding into the final shape. When processing a crosslinked polymer implant, all monomers (including the beneficial agent) and additives are added to the polymerization reaction prior to complete polymerization. Since crosslinking agent(s) is/are present, the mixture cannot be easily molded once the polymerization reaction is completed. It is preferred that the implant be shaped and molded prior to complete cure. Both continuous and batch processing procedures are applicable.

IVERMECTIN/POLY(ORTHO ESTER) IMPLANTS

Ivermectin has been incorporated into a crosslinked poly(ortho ester) erodible polymer and utilized as an implant for the control of parasites. The implant is manufactured in three stages: 1) Synthesis of a partially polymerized poly(ortho ester) paste containing the homogeneously mixed additives; 2) Dispensing of the paste into rod-shaped molds; and, 3) Curing and removal of the completely polymerized rods from the molds. The poly(ortho ester) was a condensation polymer comprised of two fundamental types of monomers: polyols (e.g., 1,6-hexanediol, tetraethylene glycol, 1,2,6-hexanetriol, ivermectin) and a diketene acetal (e.g., DETOSU). It is known that ortho ester bonds are substantially more stable to hydrolysis under basic pH conditions. The addition of an ortho ester bond stabilizer such as MgO or Mg(OH)$_2$ which results in an alkaline pH, substantially modified (slowed) the erosion process. In this invention, the beneficial agent (ivermectin) of a preferred embodiment was also a polyol and reacted as a monomer with the DETOSU to become covalently bonded within the poly(ortho ester) backbone. A statistically significant portion (1 to 100%) of the total drug covalently bonded within the polymer backbone is within the scope of the invention, with typical values of 20 to 60% bonded. This provides the advantage that the bonded ivermectin cannot diffuse out of the dosage form until it is hydrolytically cleaved from the crosslinked poly(ortho ester).

The thermal, mechanical and drug release performance of the poly(ortho ester)/ivermectin implant was controlled by the amounts of DETOSU, stabilizer, and ivermectin, and the amounts and types of polyols (diols and crosslinkers) in the formulation. To facilitate the reproducibility of the poly(ortho ester)/ivermectin implant, an inprocess control method to guide the reagent addition, mixing, molding and curing steps has been discovered. Control of the addition, mixing, molding and curing steps can be achieved by monitoring the changes in conductivity and dielectric properties of the polymerizing mixture with a dielectrometer. These changes are related to the viscosity changes as the polymerization reaction proceeds. Suitable polyols, stabilizers, and polymerization stiochimetries are as follows:

I. Polyols

1. Diols with a structure of HO-R-OH, where R is:

a. a linear hydrocarbon chain with a total carbon number of 2 to 20; specifically exemplifying such diols are 1,4-butanediol, 1,5-pentanediol, 1,6-hexanediol, 1,7-heptanediol, 1,8-octanediol, 1,9-nonanediol, 1,10-decanediol, and the like.

b. a branched hydrocarbon chain with a total carbon number between 4 and 20; specifically exemplifying such diols is 3,3-dimethylpentanediol.

c. a cyclic hydrocarbon with a total carbon number between 3 and 20; specifically exemplifying such diols is cyclohexane dimethanol.

d. a hydrocarbon residue containing heteroatoms such as oxygen, nitrogen, and/or sulfur in the main chain or oxygen, nitrogen, halide, and/or sulfur in a side group. Specifically exemplifying such diols are triethylene glycol, tetraethylene glycol, n-butyldiethanolamine, polyethylene glycols, and the like.

e. structures 1a through 1d wherein one or more of the carbons in R are replaced by silicon.

Combinations of diols with structures as described in 1a through 1e are within the scope of the invention.

2. Crosslinkers with a structure R'(OH)$_m$, where m≧3 and R' is:

a. a linear hydrocarbon chain with a total carbon number of 3 to 20.

b. a branched hydrocarbon chain with a total carbon number between 4 and 20.

c. a cyclic hydrocarbon with a total carbon number between 3 and 20.

d. a hydrocarbon residue containing heteroatoms such as oxygen, nitrogen, and/or sulfur in the main chain or oxygen, nitrogen, halide and/or sulfur in a side group.

e. structures 2a through 2d wherein one or more of the carbons are replaced by silicon.

Combinations of crosslinkers with structures as described in 2a through 2e are within the scope of the invention. Specific examples of crosslinking agents include 1,2,6-hexanetriol, tromethamine, glycerol, pentaerythritol, 2-ethyl-2-hydroxymethyl-1,3-propanediol, glucose, and 1,3,5-cyclohexanetriol. Halide is F, Cl, Br, or I.

II. Stabilizers

Oxides and hydroxides such as MgO, Mg(OH)$_2$, CaO, and Ca(OH)$_2$, carbonates and bicarbonates such as CaCO$_3$, MgCO$_3$, Na$_2$CO$_3$, and NaHCO$_3$, and organic amines such as tromethamine and triethylamine act to stabilize the polymer bonds and slow the hydrolytic breakdown.

III. Stoichiometry and Loading Specifications

The stoichiometry is defined as the ratio of equivalents of ketene acetal or vinyl ether to equivalents of hydroxyl. Stoichiometries of 0.1 to 1.5 are applicable with preferred stoichiometries of 0.7 to 1.2. Hydroxyls are contributed by diols, crosslinkers, and beneficial agents. The diols and crosslinkers may be blended in any ratio as needed to give the final desired polymer properties. Crosslinker loadings are 0.1 to 100 mole percent of the total hydroxyl equivalents contributed by reagents other than the beneficial agent with a preferred crosslinker loading of 15 to 50 mole percent. Stabilizer(s) are loaded at 0.01 to 20 percent of the total dosage form weight with preferred loadings of 1 to 10%. Beneficial agent (drug) loadings between 0.1 to 50 percent of the total dosage form weight are typical with higher and lower loads within the scope of the invention. Of the total beneficial agent load, 1 to 100% is covalently incorporated into the polymer backbone.

IV. Antioxidants

Antioxidants, for example butylated hydroxytoluene (BHT), may also be utilized in the present invention in small (usually <1% of total device weight) quantities.

V. Manufacture

Water can compete with the polyols and drug for reaction with DETOSU and skew the stoichiometry of the polymerization. Therefore, it is preferable to polymerize in a dry atmosphere using reagents with low residual water contents. All weighing, transferring, polymerizing, mixing, device curing and handling should be undertaken in a controlled low humidity environment (≦30% relative humidity is preferred).

Condensation polymerizations require pure monomers to maximize polymer molecular weights. The monomers used to fabricate the implant are polyfunctional. If there are monofunctional impurities in the reagents, the polymerization will be prematurely terminated and the erosion rate of the poly(ortho ester) may be altered. Monomers with purities ≧90% are desired and monomers of purity ≧98% are generally preferred.

It is preferred that the ivermectin/poly (ortho ester) crosslinked implant be synthesized by a batch fabrication process where the ivermectin is present during the bulk polymerization reaction. This will allow the ivermectin to be covalently incorporated into the poly(ortho ester) backbone. Example 1 describes the synthesis of such an implant. The stoichiometry of the reaction was within the preferred range of 0.7 to 1.2. The polyols (tetraethylene glycol, 1,6-hexanediol, and 1,2,6-hexanetriol), ivermectin and stabilizer (MgO) were pre-mixed. The DETOSU (diketene acetal) was then added to begin the polymerization reaction. The MgO is not soluble in this mixture. During this reaction/mixing step, the polymer simultaneously increased in molecular weight and degree of crosslinking. The resulting paste must not be completely polymerized or it will be too viscous (>2,000,000 cp at 20° C.; >200,000 cp at 50° C.) to extrude into the preferred molds. However, if the viscosity of the mixture is <200 cp (at 50° C.; <2,000 cp at 20° C.) the insoluble MgO stabilizer may settle out during cure. This could produce implants with irreproducible erosion. Typically, a viscosity of 500 to 5,000 cp at 50° C., or 5,000 to 50,000 cp at 20° C. resulted in good suspension and uniformity of the MgO and permitted room temperature molding. This viscous reaction mixture was dispensed into molds to form the implant rods. A preferred mold is fluorinated hydrocarbon polymeric tubing (e.g., FEP tubing 1.6 mm o.d., 0.7 to 0.9 mm i.d.). The dispenser was stainless steel piston and cylinder which, when loaded with the paste was hydraulically pressurized to force the paste into the mold tubes attached to the bottom of the cylinder. The filled tubes were cured in a low humidity environment at a controlled elevated temperature to complete the polymerization. The cured rods were removed from the tubes and cut to the proper length prior to packaging.

The addition, mixing, dispensing and curing steps discussed in general in the preceeding paragraph (and detailed in Example 1) were monitored and controlled by a dielectrometer. As is well known in dielectrometry, the frequency of the measurement must be chosen properly to be indicative of viscosity changes in the mixture. The measurement may contain conductivity and dipolar contributions at certain frequencies. The frequency of the measurement is chosen by known procedures in dielectrometry so that the measurement is due solely to changes in conductivity. Viscosity is inversely proportional to conductivity in such dielectrometer measurements, and is used as such here.

A dielectrometer sensor (Eumetric System III Microdielectrometer, Micromet Instruments) was taped to the inside wall of the batch mixer (Atlantic Research AR-2CV Helicone Mixer) in close proximity to the mixing blades so that the mixing process could be monitored. The mixing chamber was purged with dry nitrogen prior to proceeding with the reaction. The polyols (tetraethylene glycol, 1,6-hexanediol, and 1,2,6-hexanetriol) were placed into the batch mixer (50° C.) and stirring was initiated. As the hexanediol melted/dissolved and the polyols were blended, the log [conductivity] increased. When the rate of change in log [conductivity] reached steady-state, the preblended MgO/ivermectin powder was added to the mixer. The log [conductivity] of this mixture decreased to a steady-state rate of change of log [conductivity]. Typically this took from 8 to 15 minutes. Allowing the reagents to mix any longer once the change in log [conductivity] with time reached steady state is detrimental, since the mxiture forms a "hardened" colloidal suspension. This was easily avoided with monitoring of the dielectrometer output. The DETOSU was added to begin the polymerization once steady state of the change in log [conductivity] with time was reached.

The dielectrometer read-out is also an indication of the rate of polymerization in the batch mixer. The rate of the decrease in log [conductivity] is analogous to monitoring the rate of polymerization in a viscometer, where the viscosity increase is measured over time. In both methods, the increase in log [viscosity] was proportional to reaction time during the initial phase of polymerization (i.e., prior to the gel point and final cure). A proportional relationship exists between the rate of polymerization by viscometric monitoring and the rate of polymerization by dielectric monitoring (Example 2)

Dispensing the mixture with the viscosity sufficiently high to keep MgO uniformly suspended, yet sufficiently low to permit filling of the FEP tubes, dictates that the viscosity of the polymerizing mixture is known. The dielectrometer is a facile method for real time monitoring of this viscosity without interruption of the mixing process. There is a relationship between the actual viscosity of the mixture and the log [conductivity] measurements made with the dielectrometer (Example 3). The viscosity was periodically measured with a Haake RV12 viscometer (50° C. at 100 sec$^{-1}$). The change in log conductivity was calculated from the difference in the conductivity measurements from the start of the polymerization at 50° C. to when the viscosity sample was withdrawn. The log [conductivity] was a linear function of the ln[viscosity]. To determine the change in log [conductivity] needed to properly dispense the formulation, the rate of extrusion into 0.9 mm ID FEP tubing at a constant 1 ton force was measured. A rate of dispensing of approximately 1.5 ft/min was associated with good MgO suspension and high yeild of mold filling (i.e., long lengths of tubing could be filled). This extrusion rate was obtained when the change in log [conductivity] was approximately −1.3.

The final curing of the implant formulation can also be monitored with the dielectrometer. The cure curves show log [conductivity] values which decrease to a steady state change in log [conductivity] with time. A relationship exists between the change in log [conductivity] with time and the tensile strength of the polymer. As curing proceeds, the tensile strength, which is indicative of crosslinking (or degree of polymerization), increases to a maximum value. Likewise, as curing proceeds, the change in log [conductivity] with time decreases to a low value (approximately $-2\times10^{-4}$ log [conductivity]/minute). Over-curing the samples will result in a decrease in the tensile strength, due to degradation of the polymer. This results in an increase in the change in log [conductivity] with time. Therefore by monitoring the change in log [conductivity], an optimum cure can be achieved (i.e. maximum crosslinking).

The following Examples further illustrate the instant invention but should not be construed to limit the instant invention as put forth in the Claims which are appended hereto. Example 4 describes how the dielectrometer method increased the batch-to-batch reproductivity of manufacture, when compared to a conventional manufacturing method which did not utilize a dielectrometer.

EXAMPLE 1

Method of Manufacture

The polyols (1,2,6-hexanetriol, 1,6-hexanediol, and tetraethylene glycol) and the diketene acetal (DETOSU) were purified and dried by vacuum distillation prior to use. The drug (ivermectin) and the stabilizer (magnesium oxide) were vacuum dried. All procedures were performed in a low humidity room (Relative Humidity=10% at 69° F.).

The Atlantic Research 2CV Helicone mixer and the Micromet Instruments Eumetric System III Microdielectrometer were set up. A 14" low conductivity I/C chip dielectrometer sensor was taped to the mixer bowl in proximity to the mixing blades. The mixer was assembled, heated to 50° C., and purged with dry nitrogen for 1 hour. The dielectrometer was set to collect conductivity data at 1000 Hz, using a dipole cutoff of 0.01.

To the mixer bowl were first added 6.5366 gm of tetraethylene glycol, 6.0248 gm of 1,2,6-hexanetriol and 15.9109 gm of 1,6-hexanediol. The mixer was set at speed 6 and the dielectrometer program was started to monitor the polymerization. The change in log [conductivity] was reduced to the steady-state value of 0.004/minute after 8 minutes (log [conductivity]=−7.163), indicating that the polyols melted and homogeneously blended. At that time, a preblended mixture of magnesium oxide (2.5025 gm) and ivermectin (20.0028 gm) were slowly added to the mixer with continued stirring. The change in log [conductivity] was reduced to 0.010/minute after an additional 11 minutes (log [conductivity]=−7.470), indicating that the drug had reached steady-state solubility. The DETOSU (49.0193 gm) was then added to the mixture to begin the polymerization and the mixer speed was increased to setting 9. The polymerization proceeded at a constant rate of −0.0189 log [conductivity]/minute. The reaction was stopped 79 minutes after adding the DETOSU (log [conductivity]=−8.793) and the mixture was removed from the mixer. The change in log [conductivity] during polymerization was −1.323, while the measured viscosity of the mixture was 1200 cp (at 50° C., LVT Brookfield viscometer).

The reaction mixture was prepared for the final curing stage. The mixture was dispensed at ambient temperature (approximately 20° C.) under even hydraulic pressure (1 ton) into 25 plastic tubes (FEP 100 tubing;

0.9 mm ID, 1/16" OD). The dielectrometer sensor was removed from the batch mixer and immersed in a 5 ml Nalgene capped vial filled with the reaction mixture. The filled FEP tubing and the dielectrometer sensor/vial were placed in a 60° C. oven to complete the polymerization, i.e., cure. The dielectrometer was set to collect conductivity data at 0.001 Hz, using a dipole cutoff of 0.01. The change in log [conductivity] was reduced to a steady-state value of 0.000167/minute after 40.5 hours, indicating that the cure was completed. The samples were removed from the oven and the FEP tubing was stripped from the cured polymer rod.

The cured samples were analyzed for drug and stabilizer content, polymer crosslinking, and drug release performance. The samples contained 20.2±0.1 wt % ivermectin, with 39.2±0.5% of that total amount incorporated covalently (i.e., bound to the polymer backbone). The measured stabilizer content was 2.64±0.05 wt % MgO. The amount of 1,2,6-hexanetriol that was fully incorporated (three of its hydroxyl groups reacted) was 2.91±0.05 wt %. The tensile strength was 6.3±0.4 ksi (ASTM D-638; at 5 cm/min, 70° F.). The in vitro ivermectin dissolution rate was 5.8±0.2%/hour into a pH 5, 30% isopropanol dissolution medium (37° C.).

EXAMPLE 2

Correlation of Dielectrometer Polymerization Rate Viscometric Polymerization Rate Four individual batches of the same composition as described in Example 1 were prepared by the dielectrometer-monitored polymerization process as outlined in Example 1. These 4 batches contained different lots of reagents of various purities and water contents, and thus polymerized at different rates. The same 4 batches were prepared again using the following method to monitor the viscometric polymerization rate. The reagents (5 gm total) were weighed into the SVII measuring system cup of a Haake RV-12 viscometer at 50° C. A modified 2-paddle stirrer mixed the reagents at 100 rpm, while the increase in viscosity was monitored in realtime. Since ln[viscosity] was linear with time subsequent to the initial 10 minutes of mixing, the rate of polymerization could be monitored from the slope of the ln[viscosity] vs time plot. The following results showed that there was a good relationship between the polymerization rates of the four batches when measured by both viscometric and dielectric monitoring.

| Batch # | Viscometric Polymerization Rate (ln[viscosity]/min) | Dielectrometer Polymerization Rate (log[conductivity]/min) |
|---|---|---|
| 1 | 2.472 | −0.0706 |
| 2 | 1.161 | −0.0626 |
| 3 | 0.220 | −0.0165 |
| 4 | 0.162 | −0.0143 |

EXAMPLE 3

Correlation of Conductivity Measurements with Viscosity Measurements

Five individual batches of the same composition as described in Example 1 were prepared by the dielectrometer-monitored polymerization process as outlined in Example 1. At various times during the polymerization, samples of the reaction mixture were removed for viscosity measurement (at 50° C., 100 rpm, Haake RV-12 with SVII measuring system). The change in log [conductivity] was calculated from the difference in the conductivity at the start of the polymerization (50° C.) to when the sample was withdrawn. The results that follow showed that the log [conductivity] measured by the dielectrometer was proportional to the ln[viscosity] measured by the Haake viscometer. To determine the change in log [conductivity] needed to properly mold the mixture in 0.9 mm ID FEP tubing, the rate of dispensing at a constant 1 ton hydraulic force was measured. A dispensing rate of approximately 1.5 feet per minute was accompanied by good MgO dispersion and high tube filling yields. This optimum dispensing rate was obtained when the change in log [conductivity] was approximately −1.3.

| Batch # | ln[Viscosity] | Change in log [Conductivity] | Dispense Rate (ft/min |
|---|---|---|---|
| 1 | 5.838 | −0.742 | — |
| 1 | 6.075 | −1.016 | 2.86 |
| 1 | 6.545 | −1.301 | — |
| 2 | 6.596 | −1.312 | — |
| 3 | 6.639 | −1.343 | 1.40 |
| 1 | 6.883 | −1.511 | 1.08 |
| 4 | 7.407 | −1.710 | 0.35 |
| 1 | 7.724 | −1.990 | — |
| 5 | 7.856 | −2.054 | 0.23 |

EXAMPLE 4

Reproducibility of Batches Prepared with the Dielectrometer Monitoring Procedure Experiments were conducted to demonstrate the advantages of monitoring the polymerization with a dielectrometer. Ten individual batches of the same composition as described in Example 1 were prepared by the dielectrometer-monitored polymerization process as outlined in Example 1. Eleven other individual batches of the same composition as described in Example 1 were prepared by a similar polymerization process, but without a dielectrometer. The differences in the non-dielectrometer process were: i) the polyol melting and mixing were only monitored visually (no monitoring of polyol dissolution or mixing); ii) the ivermectin and MgO were mixed for 2 to 5 minutes prior to adding DETOSU (no monitoring of drug dissolution); iii) the polymerization mixture was dispersed into molds when the mixture "appeared to the" to be of the proper viscosity to dispense into the molds (no monitoring of the viscosity); and iv) the cure time was set at 22 hours (no monitoring of cure).

The following results showed that using the dielectrometer increased the reproducibility of manufacture of the polymer and increased the incorporation of ivermectin and 1,2,6-hexanetriol (increased the crosslinking) into the polymer. When comparing the averages and the ranges in results for the batches prepared without the dielectometer to the dielectrometer method, the following can be noted: i) the ivermectin content averaged closer to the theoretical; ii) the bound ivermectin content averaged higher and had a lower standard deviation; iii) the MgO content averaged closer to the theoretical and had a lower standard deviation; iv) the amount of 1,2,6-hexanetriol fully bonded into the polymer (as a crossliner) averaged higher, and v) the dissolution rate (at 37° C., pH 5, 30% isopropanol) averaged lower and had a lower standard deviation.

| Test Method | 10 Batches Dielectrometer Method (avg + std)* | 11 Batches Other Method (avg + std)* | 11 Batches Other Method (min-max) |
|---|---|---|---|
| Total wt % ivermectin | 19.8 ± 0.3 | 19.4 ± 0.2 | 19.0 -19.6 |
| % Ivermectin bound | 40.0 ± 1.9 | 33.7 ± 3.6 | 28.8 -39.0 |
| Wt % MgO | 2.67 ± 0.03 | 2.83 ± 0.14 | 2.63 -3.03 |
| Wt % 1,2,6-HT crosslinker | 3.1 ± 0.2 | 2.8 ± 0.3 | 2.32 -3.28 |
| Dissolution Rate (%/hr) | 6.2 ± 0.4 | 7.1 ± 0.9 | 6.06 -8.35 |
| Tensile Strength (ksi) | 6.5 ± 0.2 | 6.4 ± 0.3 | 5.94 -6.78 |

*Average of 5 replicates ± standard deviation

EXAMPLE 5

Preparation Of A Polyacetal

A polyacetal/ivermectin biodegradable polymer is produced by the dielectrometer-monitored procedures outlined in Example 1 by substituting 3,4-dihydro-2H-pyran-2-methyl-3,4-dihydro-2H-pyran-2-yl carboxylate for DETOSU (vinyl ether/hydroxyl stoichiometry=0.1 to 1.5).

What is claimed is:

1. A process for the manufacture of a bioerodible poly(ortho ester) or polyacetal polymer, which contains from 1% to 100% of a biologically active beneficial agent, which comprises:

(a) mixing, in a dry environment, a diol and a polyol having three or more hydroxyl groups until the mixture is solubilized and a uniform viscosity of solution is achieved;

(b) adding a biologically active beneficial agent having a hydroxyl functionality of two or more and a poly(ortho ester) bond stabilizer to the mixture of (a) and stirring until a uniform viscosity of solution is achieved; and (c) adding a diketene acetal or a divinyl ether to the mixture of (b) with stirring and monitoring the rate of polymerization by monitoring the change in viscosity, until the viscosity of the resulting poly(orth ester) or polyacetal is between 2,000 cp and 20,000 cp at 20° C. and 10 $sec^{-1}$;

wherein the biologically active beneficial agent is present in the poly(ortho ester) or polyacetal in a stoichiometric ratio of 0.1 to 1.5 equivalents of hydroxyl to 1 equivalent of ketene acetal of vinyl ether.

2. The process of claim 1 wherein the beneficial agent, containing a hydroxyl functionality of at least two, is selected from the group consisting of:

(a) anthelmintic agents;
(b) narcotics and narcotic antagonists;
(c) antihistamines;
(d) adrenergic agents;
(e) adrenergic blockers;
(f) sedative hypnotics;
(g) CNS agents;
(h) analeptics;
(i) antiparkinson agents;
(j) steroids;
(k) coronary vasodilators;
(l) anticoagulants;
(m) antihypercholesterolemics;
(n) antibiotics;
(o) antifungal agents;
(p) antiviral agents;
(q) bone growth promotants;
(r) anticancer agents;
(s) vitamins;
(t) antiinflammatory agents;
(u) antihypertensive agents.

3. The process of claim 2 wherein the beneficial agent is an anthelmintic selected from the group consisting of:

a) avermectins; and
b) milbemycins.

4. The process of claim 3 wherein the beneficial agent is selected from:

a) ivermectin;
b) moxidectin;
c) nemadectin;
d) milbemycin-5-oxime;
e) 4″-epi-acetylamino-4″-deoxyavermectin Bla/Blb; and
f) 22,23-dihydro-13-O-((2-methoxyethoxy)methyl)avermectin-Bl-aglycone.

5. The process of claim 4 wherein each polyol monomer is independently selected from the group consisting of:

(a) a linear hydrocarbon with 2 to 20 carbons and 2 hydroxyls;
(b) a cyclic hydrocarbon with 3 to 20 carbons and 2 hydroxyls;
(c) a linear or cyclic hydrocarbon with 3 to 20 carbons and 3 or more hydroxyls;
(d) a branched hydrocarbon with 4 to 20 carbons and 2 or more hydroxyls;
(e) acyclic or cyclic compounds of groups (a), (b), (c) and (d) containing one or more heteroatoms selected from the group consisting of:
(i) oxygen, other than as hydroxyl;
(ii) nitrogen;
(iii) halide;
(iv) sulfur;
(f) compounds of groups (a), (b), (c), (d), and (e) wherein one or more carbons are replaced by silicon.

6. The process of claim 5 wherein each polyol monomer is independently selected from the group consisting of: 1,6-hexanediol, 1,7-heptanediol, tetraethylene glycol, triethylene glycol, and 1,2,6-hexanetriol.

7. The process of claim 6 wherein the beneficial agent is ivermectin.

8. The process of claim 1 wherein a poly(ortho ester) bond stabilizer or a polyacetal bond stabilizer is selected from the group consisting of: carbonates, bicarbonates, organic amines, magnesium oxide, calcium oxide, magnesium hydroxide, and calcium hydroxide.

9. The process of claim 8 wherein the polymer is a poly(ortho ester) comprising the monomer residues of:

(a) 3,9-bis-(ethylidene)-2,4,8,10-tetraoxaspiro [5,5] undecane;
(b) ivermectin;
(c) tetraethylene glycol;
(d) 1,6-hexanediol;
(e) 1,2,6-hexanetriol.

10. The process of claim 9 wherein the poly(ortho ester) bond stabilizer is magnesium oxide.

11. The process of claim 1 wherein the viscosity of the reactants and the polymer is measured in situ as a function of conductivity with a dielectrometer, whereby reproducible control is achieved over all addition, mixing, dispersing, molding and curing steps in the manufacture of bioerodible poly(ortho ester) and polyacetal polymers.

* * * * *